US010640833B2

(12) United States Patent
Rand et al.

(10) Patent No.: US 10,640,833 B2
(45) Date of Patent: May 5, 2020

(54) RAPID DETECTION OF INFECTIOUS AGENTS

(71) Applicant: University of Florida Research Foundation, Inc., Gainesville, FL (US)

(72) Inventors: Kenneth H. Rand, Gainesville, FL (US); Herbert J. Houck, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 161 days.

(21) Appl. No.: 15/321,260

(22) PCT Filed: Jun. 26, 2015

(86) PCT No.: PCT/US2015/038114
§ 371 (c)(1),
(2) Date: Dec. 22, 2016

(87) PCT Pub. No.: WO2015/200855
PCT Pub. Date: Dec. 30, 2015

(65) Prior Publication Data
US 2017/0191117 A1 Jul. 6, 2017

Related U.S. Application Data

(60) Provisional application No. 62/017,792, filed on Jun. 26, 2014, provisional application No. 62/018,506, filed on Jun. 27, 2014.

(51) Int. Cl.
*C12P 19/34* (2006.01)
*C12Q 1/689* (2018.01)
*C12Q 1/686* (2018.01)

(52) U.S. Cl.
CPC ............ *C12Q 1/689* (2013.01); *C12Q 1/686* (2013.01); *C12Q 2600/156* (2013.01); *C12Q 2600/158* (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.3, 25.32
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,965,188 A | 10/1990 | Mullis | |
| 5,210,015 A | 5/1993 | Gelfand et al. | |
| 5,871,908 A | 2/1999 | Henco | |
| 6,635,427 B2 | 10/2003 | Wittwer | |
| 2004/0161767 A1 | 8/2004 | Baldwin et al. | |
| 2009/0081656 A1 | 3/2009 | Han et al. | |
| 2012/0035071 A1 | 2/2012 | Bergeron et al. | |

FOREIGN PATENT DOCUMENTS

| | | |
|---|---|---|
| WO | 2001/48244 | 7/2001 |
| WO | 2004/044247 | 5/2004 |
| WO | 2004/046378 | 6/2004 |
| WO | 2013/052124 | 4/2013 |
| WO | 2013/086201 | 6/2013 |

OTHER PUBLICATIONS

International Search Report and Written Opinion for PCT Application PCT/US15/038114 dated Oct. 14, 2015, pp. 1-15.
Extended European search report for EP Application 15811008.0 dated Apr. 26, 2018, pp. 1-12.
Chakravorty, S., et al, "A detailed analysis of 16S ribosomal RNA gene segments for the diagnosis of pathogenic bacteria", J. Micrbiol Methods, vol. 69, Issue 2, pp. 330-339 (2007).
Champlot, S., et al., "An efficient multistrategy DNA decontamination procedure of PCR reagents for hypersensitive PCR applications", PLoS One, vol. 5, Issue 9, 15 pages (2010).
Dierkes, C., et al., "Clinical impact of a commercially available multiplex PCR system for rapid detection of pathogens in patients with presumed sepsis", BioMed Central, vol. 9, Issue 126, 7 pages (2009).
Gaibani, P., "Blood culture systems: rapid detection—how and why", International J of Antimicrobial Agents, vol. 345, pp. S13-S15 (2009).
Haag, H., et al., "Molecular diagnosis of microbial aetiologies using SepsiTest in the daily routine of a diagnostic laboratory", Diagnostic Microbiol and Infectious Disease, vol. 76, pp. 413-418 (2013).
Kim, HC., et al, "Development of broad-range and specific 16S rRNA PCR for use in routine diagnostic clinical microbiology", J. life science, vol. 24, Issue 4, pp. 361-369 (2014).
Von Lilienfeld-Toal, M., et al., "Utility of a commercially available multiplex real-time PCR assay to detect bacterial and fungal pathogens in febrile neutropenia", J. clinical microbiol, vol. 47, Issue 8, pp. 2405-2410 (2009).
Mancini, N., et al., "Molecular diagnosis of sepsis in a neutropenic patients with haematological malignancies", J. med. microbiol., vol. 57, pp. 601-604 (2008).
Nadkarni, M., et al., "Determination of bacterial load by real-time PCR using a broad-range (universal) probe and primers set", Microbiol, vol. 148, pp. 257-266 (2002).
Rand, et al., "Taq polymerase contains bacterial DNA of unknown origin", Molecular and Cellular Probes, vol. 4, pp. 445-450 (1990).
Tsalik, E., et al., "Multiplex PCR to Diagnose bloodstream infections in patients admitted from the emergency department with sepsis", J. Clinical Microbiol., vol. 48, pp. 26-33 (2010).

(Continued)

*Primary Examiner* — Frank W Lu
(74) *Attorney, Agent, or Firm* — Timothy H. Van Dyke; Beusse, Wolter, Sanks & Maire PLLC

(57) ABSTRACT

The invention generally relates to a method for detecting a target nucleic acid in a sample. This invention is useful for detecting bacterial or viral agents in a sample, and is able to detect nucleic acids from a broad variety of, e.g., bacteria, rather than only one or a few different bacteria at a time.

16 Claims, 7 Drawing Sheets

Specification includes a Sequence Listing.

(56) References Cited

OTHER PUBLICATIONS

Wallet, F., et al., "Preliminary clinical study using a multiplex real-time PCR test for the detection of bacterial and fungal DNA directly in blood", Clin. Microbiol. Infect., vol. 16, pp. 774-779 (2009).
Wellinghausen, N., et al., "Diagnosis of bacteremia in whole-blood samples by use of a commercial universal 16S rRNA gene-based PCR and sequence analysis", J. Clinical Microbiol., vol. 47, Issue 9, pp. 2759-2765 (2009).

Primers

| | |
|---|---|
| 338-S | CTCCTACGGGAGGCAGC (SEQ ID NO:1) |
| W534-AS | ATTACCGCGGCTGCTGG (SEQ ID NO:2) |
| 1053Uni-S | GCATGGYTGTCGTCAGCTC (SEQ ID NO:3) |
| 1399-AS | GTGTGTACAAGRCCCGRGA (SEQ ID NO:4) |

Probes; for the 338/534 combo

| | |
|---|---|
| G-Ent1-Pr | TGGGCGAAAGCCTGATSCAGCCATG (SEQ ID NO:5) |
| G-Ent2-Pr | TGGGCGCAAGCCTGATSCAGCCATG (SEQ ID NO:6) |
| G+Staph-Pr | AGCAACGCCGCGTGAGTGATGAAGG (SEQ ID NO:7) |
| G+Strep-Pr | AGCAACGCCGCGTGAGTGAAGAAGG (SEQ ID NO:8) |

FIG. 1A

"Universal" Bacterial Taqman #1

HH 303-S: GGRACTGAGAYACGGYCCAR (SEQ ID NO22)
HH W534-AS: GTATTACCGCGGCTGCTGG (SEQ ID NO:23)
HH 344-AS-Pr: Fam-CACTGCTGCCTCCCGTAGGAGT-BHQ-1 (SEQ ID NO:24)

Universal Bacterial Taqman #2

HH-766-S: AACAGGATTAGATACCCTGGTAG (SEQ ID NO:9)
HH-957-AS: GCGTWKCDTCGAATTAAWCCAC (SEQ ID NO:10)
HH-898-Pr: AAAKGAATTGACGGGGRCCCGCACAAG (SEQ ID NO:11)

FIG. 1B

Universal Bacterial EvaGreen Real Time Assay

EUB 683-S   GTGTAGMGGTGRAATKCG (SEQ ID NO:12)
EUB 806-S   GGACTACCAGGGTATCTAATC (SEQ ID NO:13)

EUB 785-S   GGATTAGATACCCTGGTAGTC (SEQ ID NO:14)
EUB 939-AS  TTGTGCGGGYCCCCGTC (SEQ ID NO:15)

EUB 919-S   ACGGGGRCCCGCACAAG (SEQ ID NO:16)
EUB 1072-AS GAGCTGACGACARCCATGC (SEQ ID NO:17)

EUB 1052-S  TGCATGGYTGTCGTCAGCTC (SEQ ID NO:18)
EUB 1096-S  GGGTTGCGCTCGTTRYGG (SEQ ID NO:19)

EUB 1063-S  GTCAGCTCGTGYCGTGAG (SEQ ID NO:20)
EUB 1193-S  CGTCRTCCCCRCCTTCC (SEQ ID NO:21)

FIG.1C

Broad Range Gram Positive and Gram Negative TaqMan Assays

Gram Positive TaqMan
Gram Pos 27F-S: AGAGTTTGATCCTGGCTCAG (SEQ ID NO:25)
Gram Pos 128-AS: CGYGTTACTCACCCGTYCG (SEQ ID NO:26)
Gram Pos 76AS-RR-Probe: CATGTRTTARGCACGCGGCCAGCG (SEQ ID NO:27)

Gram Negative TaqMan Assays
27F-Universal-S: AGAGTTTGATCMTGGCTCAG (SEQ ID NO:28)
Gram Neg 27F-S: AGAGTTTGATCATGGCTCAG (SEQ ID NO:29)
Gram Neg 128Universal-AS: CATTA CTC ACC CGT YCG CC (SEQ ID NO:30)
Stenotrophomonas 128-AS: TTC CTC ACC CGT YCG CCR (SEQ ID NO:31)
Chryseobacterium 128-AS: TTR CGC ACC CGT ACG CCG (SEQ ID NO:32)

Gram Neg EnteroPsSh-Probe: CATGTGTWAGGCMTGCCGCCAGCG (SEQ ID NO:33)
Gram Neg HACEK-Probe: CATGTGTWAAGCMTGCCGCCAGCG (SEQ ID NO:34)
Stenotrophomonas -AS-Probe: CATGTGTWAGGCMTACCGCCAGCG (SEQ ID NO:35)
Chryseobacterium/Achromobacter Probe: CATGTGTWAGGCMTCCCGCTAGCG (SEQ ID NO:36)
Gram Neg- Probe 2: CATGTGTTARGCCTGCCGCCAGCG (SEQ ID NO:37)

Abbreviations:
F = Forward which is the same direction as S = Sense
S = Sense
AS = Antisense

FIG. 2

SEQUENCE LISTING

```
<160> NUMBER OF SEQ ID NOS: 37

<210> SEQ ID NO 1
<211> LENGTH: 17
<212> TYPE: DNA
<213> ORGANISM: Artificial Sequence
<220> FEATURE:
<223> OTHER INFORMATION: Probe

<400> SEQUENCE: 1
ctcctacggg aggcagc                                                    17

<210> SEQ ID NO 2
<211> LENGTH: 17
<212> TYPE: DNA
<213> ORGANISM: Artificial Sequence
<220> FEATURE:
<223> OTHER INFORMATION: Probe

<400> SEQUENCE: 2
attaccgcgg ctgctgg                                                    17

<210> SEQ ID NO 3
<211> LENGTH: 19
<212> TYPE: DNA
<213> ORGANISM: Artificial Sequence
<220> FEATURE:
<223> OTHER INFORMATION: Probe

<400> SEQUENCE: 3
gcatggytgt cgtcagctc                                                  19

<210> SEQ ID NO 4
<211> LENGTH: 19
<212> TYPE: DNA
<213> ORGANISM: Artificial Sequence
<220> FEATURE:
```

<223> OTHER INFORMATION: Probe

<400> SEQUENCE: 4
gtgtgtacaa grcccgrga                    19

<210> SEQ ID NO 5
<211> LENGTH: 25
<212> TYPE: DNA
<213> ORGANISM: Artificial Sequence
<220> FEATURE:
<223> OTHER INFORMATION: Probe

<400> SEQUENCE: 5
tgggcgaaag cctgatscag ccatg             25

<210> SEQ ID NO 6
<211> LENGTH: 25
<212> TYPE: DNA
<213> ORGANISM: Artificial Sequence
<220> FEATURE:
<223> OTHER INFORMATION: Probe

<400> SEQUENCE: 6
tgggcgcaag cctgatscag ccatg             25

<210> SEQ ID NO 7
<211> LENGTH: 25
<212> TYPE: DNA
<213> ORGANISM: Artificial Sequence
<220> FEATURE:
<223> OTHER INFORMATION: Probe

<400> SEQUENCE: 7
agcaacgccg cgtgagtgat gaagg             25

<210> SEQ ID NO 8
<211> LENGTH: 25
<212> TYPE: DNA
<213> ORGANISM: Artificial Sequence
<220> FEATURE:
<223> OTHER INFORMATION: Probe

<400> SEQUENCE: 8
agcaacgccg cgtgagtgaa gaagg             25

<210> SEQ ID NO 9
<211> LENGTH: 23
<212> TYPE: DNA
<213> ORGANISM: Artificial Sequence
<220> FEATURE:
<223> OTHER INFORMATION: Probe

<400> SEQUENCE: 9
aacaggatta gatacccrgg tag               23

<210> SEQ ID NO 10
<211> LENGTH: 22
<212> TYPE: DNA
<213> ORGANISM: Artificial Sequence
<220> FEATURE:
<223> OTHER INFORMATION: Probe

<400> SEQUENCE: 10
gcgtwkcdtc gaattaawcc ac                22

<210> SEQ ID NO 11
<211> LENGTH: 27
<212> TYPE: DNA
<213> ORGANISM: Artificial Sequence
<220> FEATURE:
<223> OTHER INFORMATION: Probe

<400> SEQUENCE: 11
aaakgaattg acggggrccc gcacaag				27

<210> SEQ ID NO 12
<211> LENGTH: 18
<212> TYPE: DNA
<213> ORGANISM: Artificial Sequence
<220> FEATURE:
<223> OTHER INFORMATION: Probe

<400> SEQUENCE: 12
gtgtagmggt graatkcg				18

<210> SEQ ID NO 13
<211> LENGTH: 21
<212> TYPE: DNA
<213> ORGANISM: Artificial Sequence
<220> FEATURE:
<223> OTHER INFORMATION: Probe

<400> SEQUENCE: 13
ggactaccag ggtatctaat c				21

<210> SEQ ID NO 14
<211> LENGTH: 21
<212> TYPE: DNA
<213> ORGANISM: Artificial Sequence
<220> FEATURE:
<223> OTHER INFORMATION: Probe

<400> SEQUENCE: 14
ggattagata ccctggtagt c				21

<210> SEQ ID NO 15
<211> LENGTH: 17
<212> TYPE: DNA
<213> ORGANISM: Artificial Sequence
<220> FEATURE:
<223> OTHER INFORMATION: Probe

<400> SEQUENCE: 15
ttgtgcgggy ccccgtc				17

<210> SEQ ID NO 16
<211> LENGTH: 17
<212> TYPE: DNA
<213> ORGANISM: Artificial Sequence
<220> FEATURE:
<223> OTHER INFORMATION: Probe

<400> SEQUENCE: 16
acggggrccc gcacaag				17

<210> SEQ ID NO 17
<211> LENGTH: 19
<212> TYPE: DNA
<213> ORGANISM: Artificial Sequence
<220> FEATURE:
<223> OTHER INFORMATION: Probe

<400> SEQUENCE: 17
gagctgacga carccatgc                                              19

<210> SEQ ID NO 18
<211> LENGTH: 20
<212> TYPE: DNA
<213> ORGANISM: Artificial Sequence
<220> FEATURE:
<223> OTHER INFORMATION: Probe

<400> SEQUENCE: 18
tgcatggytg tcgtcagctc                                             20

<210> SEQ ID NO 19
<211> LENGTH: 18
<212> TYPE: DNA
<213> ORGANISM: Artificial Sequence
<220> FEATURE:
<223> OTHER INFORMATION: Probe

<400> SEQUENCE: 19
gggttgcgct cgttrygg                                               18

<210> SEQ ID NO 20
<211> LENGTH: 18
<212> TYPE: DNA
<213> ORGANISM: Artificial Sequence
<220> FEATURE:
<223> OTHER INFORMATION: Probe

<400> SEQUENCE: 20
gtcagctcgt gycgtgag                                               18

<210> SEQ ID NO 21
<211> LENGTH: 17
<212> TYPE: DNA
<213> ORGANISM: Artificial Sequence
<220> FEATURE:
<223> OTHER INFORMATION: Probe

<400> SEQUENCE: 21
cgtcrtcccc rccttcc                                                17

<210> SEQ ID NO 22
<211> LENGTH: 20
<212> TYPE: DNA
<213> ORGANISM: Artificial Sequence
<220> FEATURE:
<223> OTHER INFORMATION: Probe

<400> SEQUENCE: 22
ggractgaga yacggyccar                                             20

<210> SEQ ID NO 23
<211> LENGTH: 19
<212> TYPE: DNA
<213> ORGANISM: Artificial Sequence
<220> FEATURE:
<223> OTHER INFORMATION: Probe

<400> SEQUENCE: 23
gtattaccgc ggctgctgg                                              19

<210> SEQ ID NO 24
<211> LENGTH: 22

```
<212> TYPE: DNA
<213> ORGANISM: Artificial Sequence
<220> FEATURE:
<223> OTHER INFORMATION: Probe

<400> SEQUENCE: 24
cactgctgcc tcccgtagga gt                                          22

<210> SEQ ID NO 25
<211> LENGTH: 20
<212> TYPE: DNA
<213> ORGANISM: Artificial Sequence
<220> FEATURE:
<223> OTHER INFORMATION: Probe

<400> SEQUENCE: 25
agagtttgat cctggctcag                                             20

<210> SEQ ID NO 26
<211> LENGTH: 19
<212> TYPE: DNA
<213> ORGANISM: Artificial Sequence
<220> FEATURE:
<223> OTHER INFORMATION: Probe

<400> SEQUENCE: 26
cgygttactc acccgtycg                                              19

<210> SEQ ID NO 27
<211> LENGTH: 24
<212> TYPE: DNA
<213> ORGANISM: Artificial Sequence
<220> FEATURE:
<223> OTHER INFORMATION: Probe

<400> SEQUENCE: 27
catgtrttar gcacgcggcc agcg                                        24

<210> SEQ ID NO 28
<211> LENGTH: 20
<212> TYPE: DNA
<213> ORGANISM: Artificial Sequence
<220> FEATURE:
<223> OTHER INFORMATION: Probe

<400> SEQUENCE: 28
agagtttgat cmtggctcag                                             20

<210> SEQ ID NO 29
<211> LENGTH: 20
<212> TYPE: DNA
<213> ORGANISM: Artificial Sequence
<220> FEATURE:
<223> OTHER INFORMATION: Probe

<400> SEQUENCE: 29
agagtttgat catggctcag                                             20

<210> SEQ ID NO 30
<211> LENGTH: 19
<212> TYPE: DNA
<213> ORGANISM: Artificial Sequence
<220> FEATURE:
<223> OTHER INFORMATION: Probe

<400> SEQUENCE: 30
```

```
cattactcac ccgtycgcc                                                    19
```

<210> SEQ ID NO 31
<211> LENGTH: 18
<212> TYPE: DNA
<213> ORGANISM: Artificial Sequence
<220> FEATURE:
<223> OTHER INFORMATION: Probe

<400> SEQUENCE: 31

```
ttcctcaccc gtycgccr                                                     18
```

<210> SEQ ID NO 32
<211> LENGTH: 18
<212> TYPE: DNA
<213> ORGANISM: Artificial Sequence
<220> FEATURE:
<223> OTHER INFORMATION: Probe

<400> SEQUENCE: 32

```
ttrcgcaccc gtacgccg                                                     18
```

<210> SEQ ID NO 33
<211> LENGTH: 24
<212> TYPE: DNA
<213> ORGANISM: Artificial Sequence
<220> FEATURE:
<223> OTHER INFORMATION: Probe

<400> SEQUENCE: 33

```
catgtgtwag gcmtgccgcc agcg                                              24
```

<210> SEQ ID NO 34
<211> LENGTH: 24
<212> TYPE: DNA
<213> ORGANISM: Artificial Sequence
<220> FEATURE:
<223> OTHER INFORMATION: Probe

<400> SEQUENCE: 34

```
catgtgtwaa gcmtgccgcc agcg                                              24
```

<210> SEQ ID NO 35
<211> LENGTH: 24
<212> TYPE: DNA
<213> ORGANISM: Artificial Sequence
<220> FEATURE:
<223> OTHER INFORMATION: Probe

<400> SEQUENCE: 35

```
catgtgtwag gcmtaccgcc agcg                                              24
```

<210> SEQ ID NO 36
<211> LENGTH: 24
<212> TYPE: DNA
<213> ORGANISM: Artificial Sequence
<220> FEATURE:
<223> OTHER INFORMATION: Probe

<400> SEQUENCE: 36

```
catgtgtwag gcmtcccgct agcg                                              24
```

<210> SEQ ID NO 37
<211> LENGTH: 24
<212> TYPE: DNA
<213> ORGANISM: Artificial Sequence

```
<220> FEATURE:
<223> OTHER INFORMATION: Probe

<400> SEQUENCE: 37
catgtgttar gcctgccgcc agcg                                          24
```

RAPID DETECTION OF INFECTIOUS AGENTS

This application claims priority to U.S. Provisional Applications 62/017,792 filed Jun. 26, 2014 and 62/018,506, filed on Jun. 27, 2014. The contents of these applications are hereby incorporated by reference in their entirety.

BACKGROUND OF THE INVENTION

Bloodstream infections (BSI) are among the most severe manifestations of bacterial disease. The detection of bacteria in blood has an important role in the diagnosis of the patient, and blood culture is still considered to be the reference method of diagnosis in a clinically suspected case of BSI.

Development of a rapid diagnostic test for detecting bacterial infection in blood or any other tissue would have a significant impact on the management of infections. For the identification of pathogens and antibiotic resistance genes in clinical samples, DNA probe and DNA amplification technologies offer several advantages over conventional methods. The organism can be detected directly in clinical samples, in donated or pooled blood, in biopsy or autopsy samples, or tissue or organs donated for transplant, thereby reducing the cost and time associated with isolation of pathogens. Also, bacterial genotypes (at the DNA level) are more stable than the bacterial phenotypes (i.e. biochemical properties). DNA-based technologies have proven to be extremely useful for specific applications in the clinical microbiology laboratory (and a method to quantify small amounts of DNA). For example, kits for the detection of fastidious organisms based on the use of hybridization probes or DNA amplification for the direct detection of pathogens in clinical specimens are commercially available.

DNA-based tests for detection and identification of bacteria could be based on the amplification of the highly conserved 16S rRNA gene followed by hybridization with internal species-specific oligonucleotides. The significance of the 16S rRNA genes is that certain sequences are conserved in virtually all species. The subsequent hybridization targets allow for amplification of species-specific oligonucleotides which are derived from species-specific bacterial genomic DNA fragments. However, ultimately, these straightforward strategies using broad-based "universal" sequences suffer from the fact that the use of normal Taq polymerase (which is contaminated with bacterial nucleic acid(s)) interferes with the detection. Contamination of the Taq polymerase with bacterial nucleic acid was first described over 20 years ago. See Rand and Houck, Molecular and Cellular Probes (1990) 4:445-450. This means if one uses primers targeting areas of the 16 S ribosomal RNA (or DNA) that are shared by many bacteria, the contamination of the Taq with these sequences becomes a limiting factor in detecting low copy numbers of bacteria. In applying such a method to the detection of bacteria in normally sterile clinical specimens, Taq enzyme contamination forces the use of primers specific to various species of bacteria, rather than allowing the use of sequences that could amplify all or many species.

SUMMARY OF THE INVENTION

The invention generally relates to a method for detecting a target nucleic acid in a sample. This invention is useful for detecting bacterial or viral agents in a sample, and is able to detect nucleic acids from a broad variety of, e.g., bacteria, rather than only one or a few different bacteria at a time.

An embodiment of the invention described herein is a method for detecting a target nucleic acid that may be present in a sample, where the method comprises contacting nucleic acids from the sample with amplification reagents, including a DNA polymerase, nucleotide monomers, and two or more primers for generating an amplicon. The primers are nucleic acids which comprise at least 10 contiguous nucleic acids from one or more of SEQ ID NOs: 1, 2, 3, 4, 9, 10, 12, 13, 14, 15, 16, 17, 18, 19, 20, 21, 22, 23, 25, 26, 28, 29, 30, 31 and 32. The sample containing the suspected target nucleic acid is incubated with the amplification reagents for a period of time and under conditions sufficient to amplify said target nucleic acid. After amplification, the presence or absence of an amplicon is detected, preferably by a specific probe. The presence of the amplicon indicates the presence of the target nucleic acid in sample. In preferred embodiments, the primers used are selected from SEQ ID NOs: 1, 2, 3, 4, 9, 10, 12, 13, 14, 15, 16, 17, 18, 19, 20, 21, 22, 23, 25, 26, 28, 29, 30, 31 and 32. Most preferred primers are selected from SEQ ID NOs: 25, 26, 28, 29, 30, 31, and 32.

In preferred embodiments, the amplification reagents also contain at least one detectable probe specific for a sequence portion of the amplicon. The embodiments of the invention also include methods where the detection is performed using a detectable probe and detecting hybridization of said detectable probe to the amplicon. Preferred probes are selected from SEQ ID NOs: 5, 6, 7, 8, 11, 24, 27, 33, 34, 35, 36, and 37, or an effective fragment thereof.

In preferred embodiments, the target in the sample comprises DNA or RNA. Where the sample comprises RNA, the amplification reagents preferably further comprise cleaned reverse transcriptase. In other embodiments, the amplification reagents also can further comprise a reverse transcriptase or a cleaned reverse transcriptase. The cleaned reverse transcriptase can be produced by enzymatic, chemical, or physical treatment of contaminated reverse transcriptase (including the physical separation of the reverse transcriptase from contaminating nucleic acid).

In certain preferred embodiments of the inventive method, amplification comprises real-time PCR amplification or standard PCR. In such embodiments and in other embodiments of the invention, the amplification reagents comprise a sequence-specific DNA probe consisting of oligonucleotides that are labelled with a fluorescent reporter, most preferably where this fluorescent reporter is a non-specific fluorescent dye that intercalates with any double-stranded DNA.

In some embodiments, the amplification reagents comprise a control target nucleic acid, which can serve as a control for the amplification reaction. This control target nucleic acid can be a quantitative control nucleic acid.

Further embodiments of the invention encompass kits for performance of the method. Therefore, an embodiment of the invention comprises a kit for performance of the methods discussed above, which comprises amplification reagents comprising a DNA polymerase, nucleotide monomers, and two or more primers for generating an amplicon, wherein said primers comprise at least a 10 contiguous nucleic acids from one or more of SEQ ID NOs: 1, 2, 3, 4, 9, 10, 12, 13, 14, 15, 16, 17, 18, 19, 20, 21, 22, 23, 25, 26, and 28, 29, 30, 31, and 32. The kits also can optionally contain a probe selected from the group consisting of SEQ ID Nos. 5, 6, 7, 8, 11, 24, 27, 33, 34, 35, 36, and 37. This probe preferably is a detectable probe. Kits according to the invention also preferably contain a cleaned reverse transcriptase and/or a control nucleic acid.

BRIEF DESCRIPTION OF THE DRAWINGS

FIGS. 1A, 1B and 1C provide sequences of exemplary primers and probes relevant to the disclosed embodiments.

FIG. 2 provides the sequences of select preferred primers and probes for detection of Gram positive and Gram negative bacterial species. These primers and probes can be used with the same methods described for any of the other sequences.

DETAILED DESCRIPTION

Introduction

Figure 3:
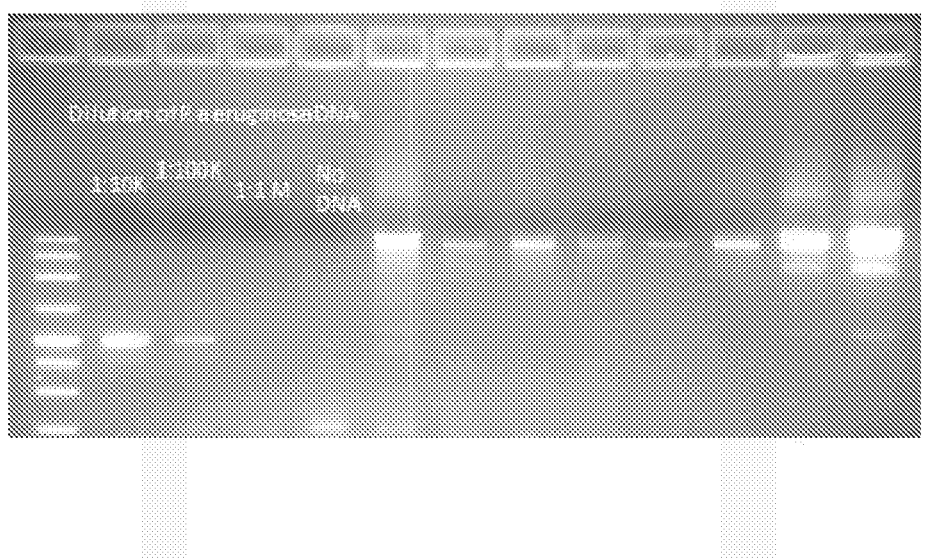
FIG. 3 is a photograph of a gel from an evaluation of a PCR product made using SEQ ID NOs: 1 and 2 as primers. Lanes 1-4 show dilutions of the sample and Lane 5 has no DNA

An aspect of the present invention is a method for amplifying and detecting a target nucleic acid in a sample, wherein an amplification of the nucleic acids in said sample is carried out, preferably using PCR and a set of broad-based "universal" primers and probes. The target nucleic acid is typically a "universal" sequence of a target infectious agent, which can be any convenient sequence that is present in a wide range of bacterial species, also referred to here as a broad-based sequence, amplified by a broad-based or "universal" primer set. With respect to bacteria, the typical target nucleic acid preferably is 16S RNA.

This amplification typically involves a DNA polymerase, nucleotide monomers, primers for generating an amplicon and at least two detectable probes specific for different sequence portions of said amplicon. Detection of the obtained amplicon can be brought about by detecting hybridization of probe(s) to a sequence portion(s) of the amplicon.

Furthermore, a kit is provided for amplifying and detecting a target nucleic acid that may be present in a sample, said target nucleic acid comprising a "universal" sequence of an infectious agent. The kit comprises amplification reagents comprising a DNA polymerase, nucleotide monomers, primers for generating an amplicon and at least one detectable probe specific for a sequence portion of said amplicon. In addition, reaction mixtures are provided for amplifying and detecting a target nucleic acid that maybe present in a sample. The reaction mixtures comprise a sample or a portion of a sample, and amplification reagents comprising a DNA polymerase, nucleotide monomers, primers for generating an amplicon and at least one detectable probe specific for the "universal" sequence of said amplicon.

SUMMARY AND DEFINITIONS

In the context of the present invention, the term "amplifying" or "amplification" a nucleic acid sequence generally refers to the production of a plurality of nucleic acid copy molecules having that sequence from a target nucleic acid wherein primers hybridize to specific sites on the target nucleic acid molecules in order to provide an initiation site for extension by a polymerase, e.g., a DNA polymerase. Amplification can be carried out by any method generally known in the art, such as but not limited to: standard PCR, real-time PCR, long PCR, hot start PCR, qPCR, Reverse Transcription PCR and Isothermal Amplification.

A "cleaned polymerase," in the context of the present invention, refers to a polymerase, e.g., as DNA polymerase or Taq polymerase, which has been treated to remove contaminating nucleic acids that could or do interfere with the assay by cross-hybridizing with the primers amplifying the target sequence, so that they are amplified and subsequently detected, providing a false positive. Preferably, all detectable potentially interfering contaminating material is removed, or at least about 99.9% of such material, or 99%, 98%, 97%, 96%, 95%, 90%, 85% or 80% of such material. Polymerases used in the context of this invention preferably are cleaned and have no detectable interfering nucleic acid material, or at least a small enough amount of such material to avoid interference with amplification and/or detection of the target sequence to the desired sensitivity. In other words, the primers most preferably should not amplify any material from the Taq polymerase or other polymerase used for amplification. Such a degree of "cleaning" is readily discernable to the person of skill in practicing the invention. A "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined. The target nucleic acid may be a genomic sequence, e.g. part of a specific gene, or RNA. In other embodiments, the target nucleic acid may be viral or bacterial. Target nucleic acids can comprise subgroups with distinct sequence variations or distinct individual mutations in the amplicon region. This is especially the case for nucleic acids of pathogens like viruses which show significant genetic variation due to high mutation or recombination rates and lacking repair mechanisms.

In the context of the present invention, the target sequence is a "broad-based" or "universal" target sequence. As used to in the present application, these terms and their cognates refer to a sequence in bacteria or viruses (or other cells) that is present in a large number of species and therefore can be used to detect a large number of species and to detect the presence of, e.g., bacteria in general, in a sample. The targets which are useful for the present invention can be any sequence which is present in a wide range of bacteria or other species to be detected, or in certain groups or subgroups of bacteria or viruses which are to be detected by the assay. The advantage of such targets is that it is not necessary to perform multiple tests on a sample using multiple targets, one for each suspected species, for example, to determine whether bacteria are present or not. This method was not possible using prior art methods, particularly for sensitive assays detecting low levels of bacteria, because primers aimed at amplifying and detecting broadly-based targets also detected the contaminating nucleic acids in Taq polymerase, resulting in a false positive. In summary, the broad range or "universal" primer sets of the invention here detect many different species of the desired groups or subgroups, or very broadly, to virtually any bacteria generally, the "universal" target amplification and detection serving as a proxy for the detection of bacteria. Preferred methods are for the detection of bacteria in a sample. The most preferred target sequence is a sequence from 16S RNA.

The term "amplicon" refers to a polynucleotide molecule (or collectively the plurality of molecules) produced following the amplification of a particular target nucleic acid. The amplification method used to generate the amplicon can be any suitable method, for example, a PCR method. An amplicon is typically, but not exclusively, a DNA amplicon. An amplicon can be single-stranded or double-stranded, or a mixture thereof in any concentration ratio. In an embodiment of the invention, the amplicon consists of subpopulations with heterogeneous sequences between the primer sequences. It can be favorable to monitor the amplification reaction in real time, i.e. to detect the target nucleic acids and/or their amplicons during the amplification itself. The term "detecting" or "detection" as used herein relates to a test aimed at assessing the presence or absence of a target nucleic acid in a sample.

The method set out above is in some embodiments based on detection methods using Fluorescence Resonance Energy Transfer (FRET) between a donor fluorescent moiety and an acceptor fluorescent moiety. In these embodiments, the detectable probes specific for different sequence portions of the amplicon are FRET probes. A representative donor fluorescent moiety is fluorescein, and representative corresponding acceptor fluorescent moieties include LC-Red 640, LC-Red 705, CY5, and CY5.5.

Typically, detection includes exciting the sample at a wavelength absorbed by the donor fluorescent moiety and visualizing and/or measuring the wavelength emitted by the corresponding acceptor fluorescent moiety. In the method described above, detection is in some embodiments followed by quantitating the FRET. In the context of the invention, the terms "FRET" or "fluorescent resonance energy transfer" or "Foerster resonance energy transfer" can be used interchangeably and refer to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used donors are e.g. fluoresceins, coumarins, cyanines and rhodamines. Commonly used quenchers are DABCYL and TAMRA. Commonly used dark quenchers include BlackHole Quenchers™ (BHQ), (Biosearch Technologies, Inc., Novato, Calif.), Iowa Black™ (Integrated DNA Tech., Inc., Coralville, Iowa), and BlackBerry™ Quencher 650 (BBQ-650) (Berry & Assoc., Dexter, Mich.). Any of these compounds, or any convenient donor and acceptor pairs known in the art can be and are contemplated for use with the invention.

A common format of FRET technology utilizes two hybridization probes forming a HybProbe pair. Each probe can be labeled with a different fluorescent moiety. The probes are generally designed to hybridize in close proximity to each other in a target DNA molecule (e.g., an amplification product). A donor fluorescent moiety such as fluorescein is excited at 470 nm by the light source e.g. a LIGHTCYCLER® instrument. During FRET, the fluorescein transfers its energy to an acceptor fluorescent moiety such as e.g. LIGHTCYCLER®-Red 640 (LC®-Red 640) or LIGHTCYCLER®-Red 705 (LC®-Red 705). The acceptor fluorescent moiety then emits light of a longer wavelength, which is detected by the optical detection system of the LIGHTCYCLER® instrument. Efficient FRET can only take place when the fluorescent moieties are in direct local proximity (usually about 1 to 5 nucleotides distance) and when the emission spectrum of the donor fluorescent moiety overlaps with the absorption spectrum of the acceptor fluorescent moiety. The intensity of the emitted signal can be correlated with the number of original target nucleic acid molecules. In the context of the present invention, as also appreciated by the person skilled in the art, a HybProbe pair is to be understood as a functional unity and thus a single probe, since the two members of such a pair have to be used together.

Detection of amplicon formation on Cobas®TaqMan® systems utilizes a single-stranded hybridization probe (also termed "5'-nuclease probe"). The term "5'-nuclease probe" refers to an oligonucleotide that comprises at least one light emitting labeling moiety and that is used in a 5'-nuclease reaction to effect target nucleic acid detection. In some embodiments, for example, a 5'-nuclease probe includes only a single light emitting moiety (e.g., a fluorescent dye, etc.). In certain embodiments, 5'-nuclease probes include regions of self-complementarity such that the probes are capable of forming hairpin structures under selected conditions. To further illustrate, in some embodiments a 5'-nuclease probe comprises at least two labeling moieties and emits radiation of increased intensity after one of the two labels is cleaved or otherwise separated from the oligonucleotide. In certain embodiments, a 5'-nuclease probe is labeled with two different fluorescent dyes, e.g., a 5' terminus reporter dye and a 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched at least in part. During an extension step of a polymerase chain reaction, for example, a 5'-nuclease probe bound to a template nucleic acid is cleaved by the 5' to 3' nuclease activity of, e.g., a Taq polymerase or another polymerase having this activity like e.g. the Z05 polymerase, such that the fluorescent emission of the reporter dye is no longer quenched. Exemplary 5'-nuclease probes are described in, e.g., U.S. Pat. No. 5,210,015. In some embodiments, a 5' nuclease probe may be labeled with two or more different reporter dyes and a 3' terminus quencher dye or moiety. Typical fluorescent dyes used in this format are for example, among others, FAM, HEX, CY5, JA270, Cyan500 and CY5.5.

In an embodiment of the method described above, the detectable probes specific for different sequence portions of the amplicon are 5'-nuclease probes. The detectable probes can hybridize to the same or to different strands of a double-stranded amplicon.

In some embodiments of the method described above, at least two detectable probes hybridize to different strands of said amplicon. In this case, the skilled person is provided with increased flexibility with regard to selecting the primer and probe sequences and thus binding sites on the respective amplicon. For instance, in the case of secondary structure formation due to a specific sequence within an oligonucleotide, it can be important to be able to switch to a different sequence and thus to a different binding site on said amplicon. Further, if the detectable probes bind to different strands, such as a first probe to the sense strand and a second probe to the antisense strand of a double-stranded amplicon, the risk of those probes interfering with each other at their respective binding sites is reduced.

In further embodiments of the method described above, at least two detectable probes hybridize to the same strand of said amplicon. Thus, in an embodiment of the method described above, the detectable probes specific for different sequence portions of said amplicon hybridize to the amplicon with no more than 100 bases distance to each other, in some embodiments from 1, 5, 10, 20, 30, 40 or 50 bases, to 60, 70, 80, 90, or 100 bases distance to each other. In some embodiments, the distance is from 40 to 80, or from 50 to 70, or from 55 to 60 bases, or it is 58 bases. In this context, "distance" means the number of bases of the amplicon lying between those bases of the amplicon to which the detectable probes hybridize in case they hybridize to the same strand. If they hybridize to different strands, the distance is calculated accordingly, wherein each base of one strand of a double-stranded amplicon has a corresponding base on the other strand with which it forms a base pair.

In some embodiments, detection is performed after each cycling step of a cycle-based amplification technique such as PCR. In some embodiments, detection is performed in real time. By using commercially available real-time PCR instrumentation (e.g., LightCycler® or TaqMan®), PCR amplification and detection of the amplification product can be combined in a single closed cuvette with considerably reduced cycling time. Since detection occurs concurrently with amplification, real-time PCR methods obviate the need for manipulation of the amplification product, and diminish the risk of cross-contamination between amplification products. In both detection formats described above, the intensity of the emitted signal can be principally correlated with the number of original target nucleic acid molecules.

A "sample" is any material that can be subjected to a diagnostic assay and generally refers to the medium possibly containing the target nucleic acid. The "sample" is in some embodiments derived from a biological source. The sample can be e.g. a clinical sample. In some embodiments, said sample is derived from a human and is a body liquid or biopsy sample. In some embodiments of the invention, the sample is human whole blood or serum, blood plasma, urine, sputum, sweat, breast milk, semen, intraocular fluid, genital or buccal or nasal swabs, pipettable stool, solubilized tissue samples, or spinal fluid or the like. A sample can be pipetted or converted to a pipettable form, such that the term "sample" comprises homogeneous or homogenized liquids, but also emulsions, suspensions and the like. A sample may also e.g. be an originally solid sample (i.e. tissue sample) which is subjected to a solubilization treatment for extraction and purification of nucleic acids.

A "polymerase" as used herein is an enzyme capable of synthesizing nucleic acids from smaller elements such as nucleotides. In some embodiments, the nucleic acid polymerase is a DNA polymerase. In some embodiments, the polymerase is a thermostable polymerase. The term "thermostable polymerase" refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188. As used herein, a thermostable polymerase is suitable for use in a temperature cycling reaction such as the polymerase chain reaction ("PCR") and such polymerases are known to those of skill in the art.

Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. For amplification purposes, said nucleotides are present in monomeric form, therefore they are also referred to as "nucleotide monomers" in the context of the present invention. Often, such nucleotide monomers used by polymerases such as e.g. thermostable DNA polymerases are e.g. nucleoside triphosphates, or nucleoside tetraphosphates, or the like. Thermostable DNA polymerases from thermophilic bacteria include, e.g., DNA polymerases from *Thermotoga maritima*, *Thermus aquaticus*, *Thermus thermophilus*, *Thermus flavus*, *Thermus filiformis*, *Thermus* species Sps17, *Thermus* species Z05, *Thermus caldophilus*, *Bacillus caldotenax*, *Thermotoga neopolitana*, and *Thermosipho africanus*.

The term "primer" is used herein as known to the expert skilled in the art and refers to oligomeric compounds, primarily to oligonucleotides, but also to modified oligonucleotides, that are able to prime DNA synthesis by a template-dependent DNA polymerase, i.e. the 3'-end of the primer provides a free 3'-OH group where further nucleotides may be attached by a template-dependent DNA polymerase establishing 3'- to 5'-phosphodiester linkage whereby deoxynucleoside triphosphates are used and whereby pyrophosphate is released.

A "probe" or "detectable probe" also denotes a natural or modified oligonucleotide. As known in the art, a probe serves the purpose of providing a means for detecting an analyte or amplificate. In the context of the invention, probes can e.g. be used to detect the amplificates of the target nucleic acid and/or a control nucleic acid. For the purpose of detectability, probes typically carry labels. Any suitable probe or labeled probe known in the art which is suitable and convenient for the assay being used is contemplated for use with the invention.

In some embodiments of the method, the at least two detectable probes specific for different sequence portions of said amplicon carry the same type of label and thus the signal originating from the individual probe cannot be distinguished. In other embodiments, they carry different labels emitting signals of different wavelengths such that the signals from the at least two probes can be distinguished with the appropriate instrumentation.

"Labels", often referred to as "reporter groups", generally are groups that make a nucleic acid, in particular oligonucleotides or modified oligonucleotides, as well as any nucleic acids bound thereto, distinguishable from the remainder of the sample. Useful labels in the context of the invention are e.g. fluorescent labels, which may be fluorescent dyes such as for instance a fluorescein dye, a rhodamine dye, a cyanine dye, or a coumarin dye. Useful fluorescent dyes in the context of the invention are e.g. FAM, HEX, JA270, CAL635, Coumarin343, Quasar705, Cyan500, CY5.5, LC-Red 640, LC-Red 705, TAMRA, SYBR, EvaGreen or CY5. However, any label which can render the amplified target sequence nucleic acid be detected can be used for methods according to this invention.

In the context of the invention, any primer and/or probe may be chemically modified, i.e. the primer and/or the probe comprise a modified nucleotide or a non-nucleotide compound. The probe or the primer is then a modified oligonucleotide.

As known by the person skilled in the art, the term "specific" in the context of primers and probes implies that a primer or probe "specific" for a distinct nucleic acid binds to said nucleic acid under stringent conditions. In some embodiments the probes used in the context of the invention are at least 80% or 90%, 95%, 98%, 99% or 99.9% identical to the different sequence portions of the amplicon. In another embodiment, the probe sequences comprise at least 10 contiguous nucleotides of a sequence selected from the group consisting of SEQ ID NOs: 5, 6, 7, 8, 11, 24, 27, 33, 34, 35, 36, and/or 37, or the corresponding complementary nucleic acid sequences thereof, and the primers comprise at least 10 contiguous nucleotides of any of the appropriate SEQ ID NOs discussed herein, preferably SEQ ID NOs: 1, 2, 3, 4, 9, 10, 12, 13, 14, 15, 16, 17, 18, 19, 20, 21, 22, 23, 25, 26, 28, 29, 30, 31, and 32, and most preferably SEQ ID NOs: 25, 26, 28, 29, 30, 31 and 32. In some embodiments, the selected primer sequences consist of 10 to 60 nucleotides, or of 10 to 40 nucleotides, or of the exact sequences selected from said SEQ ID NOs: 1, 2, 3, 4, 9, 10, 12, 13, 14, 15, 16, 17, 18, 19, 20, 21, 22, 23, 25, 26, 28, 29, 30, 31, and 32 or their complementary nucleic acid sequences. The skilled person understands that, in the sense of the invention, a probe pair forming a functional entity such as e.g. a Hybprobe pair used in the LightCycler® instrument is not "at least two detectable probes specific for different sequence portions of said amplicon". The two Hybprobes of a pair are regarded as a unit and can only be detected together, while each of the at least two probes in the context of the invention is detectable alone.

In a specific embodiment, one or more of probes 5-8 may be implemented to detect an amplicon produced using primer pair of SEQ ID NO. 1 and 2. When other primers as taught herein are used, one skilled in the art will be able to determine probes that hybridize with the amplicon produced using the other primers such as SEQ ID Nos 3 and 4. Persons of skill also can determine or produce probes that hybridize with the amplicon produced with the preferred primers provided in FIG. 2 herein. This can be determined through sequence analysis from databases and tested by conventional methods such as TaqMan and melting curve analysis. Preferred broad range primers for detecting Gram positive bacteria are SEQ ID NOs: 25 and 26. Preferred broad range primers for detecting Gram negative bacteria are SEQ ID NOs: 28, 29, 30, 31, and 32. Probes for use with these primers are provided in FIG. 2. Preferred probes are SEQ ID NOs: 27 (Gram positive), 33, (Gram negative) 34 (Gram negative), and 37 (Gram negative).

Melting curve analysis is useful in the study of various substances. In particular, nucleic acids have been studied extensively through melting curves, where differences in melting curves can indicate different nucleic acid sequences. Persons of skill are familiar with these methods, however a brief summary of the techniques follows. A melting curve may be obtained by applying a gradient of energy to (e.g., heating) a solution containing a nucleic acid product. As energy is added and the temperature of the solution increases, the product may denature (e.g., disassociate). While the examples make reference to increase in temperature, other methods of melting, e.g., a gradient changing the ionic concentration, are known in the art. A melting curve may be generated by measuring the extent to which this disassociation occurs as a function of temperature (or other melting gradient). See, e.g., U.S. Pat. No. 5,871,908, herein incorporated by reference. Therefore, as used herein, a melting curve may refer to any dataset comprising measurements quantitating the extent to which a compound changes its structure in response to a melting gradient, such as temperature or ionic concentration (e.g., the extent to which strands in a nucleic acid product disassociate as a function of the energy gradient applied thereto).

In some embodiments, the disassociation may be measured electro-optically. The nucleic acid product (or other compound) may be placed into a solution comprising a binding dye. The binding dye may be adapted to emit electro-optical (EO) radiation when bound to double-stranded DNA (dsDNA). As the product disassociates, the binding dye may cease emitting EO radiation (or, as discussed below, may emit EO radiation at a reduced level). Accordingly, a melting curve can be generated by acquiring measurements of the EO radiation (fluorescence) emitted from the solution as energy is applied thereto (e.g., as the temperature of the solution is increased). Moreover, it is understood that the disclosure is not limited to embodiments in which the fluorescence decreases during melting; in some embodiments, such as those using G-quenching single labeled probes, the fluorescence signal may increase upon melting (see, e.g., U.S. Pat. No. 6,635,427).

A melting curve may, therefore, comprise a series of EO radiation measurements (e.g., measurements of the fluorescence emitted from the solution) as a function of temperature. However, the teachings of this disclosure may be applied to other melting curves comprising disassociation measurements acquired in other ways. Accordingly, this disclosure should not be read as limited to any particular method and/or technique for acquiring melting curve data {e.g., for acquiring measurements quantifying nucleic acid disassociation as a function of the energy applied to the solution).

As discussed above, information regarding the structure of a nucleic acid product may be inferred from a melting curve. As such, melting curve data can be used to examine polymerase chain reaction (PCR) products. A melting curve of a PCR product can be acquired by heating a product of a PCR reaction in the presence of a binding dye, which, as discussed above, may be adapted to fluoresce more strongly when bound to dsDNA than when bound to single-stranded lengths of DNA (ssDNA). Therefore, at relatively low temperatures, where the PCR product may exist primarily as dsDNA, the solution may fluoresce at a relatively high level. As the temperature of the solution is increased, the product may disassociate (e.g., denature) into two (2) strands of ssDNA, which may cause the solution to fluoresce at a lower level. Within a narrow temperature window, the PCR product may undergo a phase transition from a dsDNA state to a ssDNA state. As described above, this transition may reduce the fluorescence emitted by the solution. The temperature window in which this transition occurs may be referred to as a melting region, a melting transition, and/or a melting window.

Furthermore, in the context of the invention the term "overlap" means that two or more oligonucleotides, in particular the at least two detectable probes mentioned supra, comprise identical (when bound to the same strand) or complementary (when bound to different strands) sequence stretches. The probes used in the method described above in some embodiments do not overlap and thus do not compete in binding to a specific site on the amplicon. When bound, said two or more probes are hybridized to different sequence stretches of said amplicon. The detectable probes used in the context of the invention are advantageous as compared to overlapping probes.

The term "hybridize" or "hybridization" generally refers to the base-pairing between different nucleic acid molecules consistent with their nucleotide sequences. The terms "hybridize" and "anneal" can be used interchangeably.

As known by the skilled person, a measure for the inclusivity is the detection of viral subgroups and isolates carrying mutations with equivalent sensitivity as the standard isolates not significantly deviating from the consensus sequence. Sensitivity of an assay is the LOD (Limit Of Detection), referring to the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is a copy of the respective nucleic acid. "IU/ml" stands for "International units/ml", referring to the WHO standard. The WHO standards are generally built from a standard isolate with a genome close to the consensus sequence.

In a first embodiment, the present invention relates to a method for amplifying and detecting a target nucleic acid that may be present in a sample, said target nucleic acid, said method comprising the steps of:
  a) contacting nucleic acids from said sample with amplification reagents comprising a DNA polymerase, nucleotide monomers, and two or more primers for generating an amplicon, wherein said primers comprise at least a 10 contiguous nucleic acids from at least two of the following primers: SEQ ID NOs:1, 2, 3, 4, 9, 10, 12, 13, 14, 15, 16, 17, 18, 19, 20, 21, 22, 23, 25, 26, 28, 29, 30, 31, 32, and optionally at least one detectable probe specific for a sequence portion of the amplicon;
  b) incubating said nucleic acids with said amplification reagents for a period of time and under conditions sufficient for an amplification reaction to occur; and
  c) optionally detecting the presence or absence of said amplicon by detecting hybridization of said detectable probe to the sequence portion, wherein the presence of said amplicon is indicative of the presence of said target nucleic acid in said sample.

In a specific embodiment, the primer pair used is SEQ ID NOs: 1 and 2. When SEQ ID NOs: 1 and 2 are used as the primer pair, one or more probes of SEQ ID NOs: 5, 6, 7 and 8 may be used. In another embodiment, the primer pair used is SEQ ID NOs: 22 and 23, and the probe used is SEQ ID NO: 24. In another specific embodiment, the primer pair of SEQ ID NOs: 9 and 10 is used and the probe used is SEQ ID NO: 11. In a preferred specific embodiment, the primer pair used is SEQ ID NOs: 25 and 26, and the probe used is SEQ ID NO: 27. In as second preferred specific embodiment, the primer pair used is SEQ ID NOs: 28 or 29 and 30, 31 or 32 and the probe used is one or more of SEQ ID NOs: 33, 34, 35, 36 and 37. Detection may also be achieved using other conventional techniques in the art such as gel electrophoresis, melting curve analysis and/or intercalating dyes such as but not limited to, SyBr Green or Eva Green. Use of primer pairs of SEQ ID NOs: 3 and 4, 12 and 13, 14 and 15, 16 and 17, 18 and 19, and 20 and 21 would typically involve such conventional methods for detection.

Those skilled in the art will understand that a probe may not be necessary to detect the PCR product. The PCR product can be subject to gel electrophoresis and detected visually using a dye agent. In a more specific embodiment, the primers used to generate the PCR product are SEQ ID Nos. 1 and 2, or 3 and 4.

In some embodiments of the invention, one or more steps of the method described above are automated. In further embodiments, all steps are automated. Automated systems provide a number of advantages as compared to manual methods, particularly in the field of in vitro diagnostics. The skilled person is enabled to leave the system after initiating the method, thus reducing hands-on time and providing the basis for a high sample throughput in a relatively short period of time, yet at the same time increasing reproducibility of the result. This is especially, but not only, an important feature in situations with a high number of clinical samples to be screened as quickly as possible, such as e.g., in bloodbanks.

A primer suitable for annealing to an RNA template may also be suitable for amplification by PCR. For PCR, a second primer, complementary to the reverse transcribed cDNA strand, provides an initiation site for the synthesis of an extension product.

In the amplification of an RNA molecule by an RNA-dependent DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "one-step real-time PCR", in this context, may refer to a reaction without reverse transcription step if target nucleic acid is DNA or a reaction including a reverse transcription step if target nucleic acid is RNA. By "one-step real-time PCR" it is meant that following the reverse transcription (RT) step, there is no need to open the reaction vessel or otherwise adjust reaction components prior to the amplification step. In a non-one-step real-time PCR reaction, following reverse transcription and prior to amplification one or more of the reaction components such as the amplification reagents are e.g. adjusted, added, or diluted, for which the reaction vessel has to be opened, or at least its contents have to be manipulated. Both one-step real-time PCR and non-one-step real-time PCR embodiments are contemplated for use with the invention as an example of useful amplification methods, and thus are within the scope of the invention.

According to a more specific embodiment, the method comprises a method described above, further comprising prior to step a) the steps of:
  i) combining together a solid support and said sample for a period of time and under conditions sufficient to permit nucleic acids comprising said target nucleic acid to be immobilized on said solid support;
  ii) isolating said solid support from the other material present in the sample in a separation station;
  iii) purifying the nucleic acids in the separation station by separating the sample from the solid support and washing the solid support one or more times with a wash buffer.

In the context of the invention, the term "solid support" as used herein relates to any type of solid support to which the analyte is capable of binding, either directly and non-specifically by adsorption, or indirectly and specifically. Indirect binding may be binding of an analyte to an antibody immobilized on the solid support, or binding of a tag to a tag binding compound, e.g. binding of 6×His tags to Ni-chelate. When the analyte is a nucleic acid, such indirect binding may be by binding to a capture nucleic acid probe which is homologous to a target sequence of the nucleic acid of interest. Thus, using capture probes attached on a solid support, a target analyte, or a target nucleic acid, can be separated from non-target material, or non-target nucleic acid. Such a capture probe is immobilized on the solid support. Solid support material may be a polymer, or a composition of polymers. Other types of solid support material include magnetic silica particles, metal particles, magnetic glass particles, glass fibers, glass fiber filters, filter paper etc., while the solid support material is not limited to these materials.

"Immobilize", in the context of the invention, means to capture objects such as nucleic acids in a reversible or irreversible manner. Particularly, "immobilized on the solid support material", means that the object or objects are associated with the solid support material for the purpose of their separation from any surrounding media, and can be recovered e.g. by separation from the solid support material at a later point. In this context, "immobilization" can e.g. comprise the adsorption of nucleic acids to glass or other suitable surfaces of solid materials as described supra. Moreover, nucleic acids can be "immobilized" specifically by binding to capture probes, wherein nucleic acids are bound to essentially complementary nucleic acids attached to a solid support by base-pairing. In the latter case, such specific immobilization leads to the predominant binding of target nucleic acids.

A "separation station" is a device or a component of an analytical system allowing for the isolation of the solid support from the other material present in the sample. Such a separation station can e.g. comprise, while it is not limited to these components, a centrifuge, a rack with filter tubes, a magnet, or other suitable components. In some embodiments, the separation station comprises one or more magnets. In certain embodiments, one or more magnets are used for the separation of magnetic particles, such as e.g. magnetic glass particles, as a solid support. If, for example, the sample and the solid support material are combined together in the wells of a multiwell plate, then one or more magnets comprised by the separation station can e.g. be contacted with the sample itself by introducing the magnets into the wells, or said one or more magnets can be brought close to the outer walls of the wells in order to attract the magnetic particles and subsequently separate them from the surrounding liquid.

In the sense of the invention, "purification", "isolation" or "extraction" of nucleic acids relate to the following: Before nucleic acids may be analyzed in a diagnostic assay e.g. by amplification, they typically have to be purified, isolated or extracted from biological samples containing complex mixtures of different components. For the first steps, processes may be used which allow the enrichment of the nucleic acids.

A "wash buffer" is a fluid that is designed to remove undesired components, especially in a purification procedure. Such buffers are well known in the art. In the context of the purification of nucleic acids, the wash buffer is suited to wash the solid support material in order to separate the immobilized nucleic acid from any unwanted components. The wash buffer may, for example, contain ethanol and/or chaotropic agents in a buffered solution or solutions with an acidic pH without ethanol and/or chaotropic agents as described above. Often the washing solution or other solutions are provided as stock solutions which have to be diluted before use.

Summarizing, by applying the steps i) to iii) of the method described above, the nucleic acids including the target nucleic acid that may be present in the sample are separated from the remainder of the sample, such that the risk of inhibition of the subsequent steps by any potentially interfering substances in said sample is reduced.

For downstream analysis, the nucleic acids may subsequently be eluted from the solid support e.g. by means of an appropriate elution buffer. Such an elution buffer may, e.g., be distilled or deionized water or aqueous salt solutions, such as Tris buffers like Tris HCl, or HEPES, or other suitable buffers known to the skilled artisan.

In some embodiments, the solid support is present in the amplification reaction mixture during amplification and in some embodiments also detection.

In some embodiments of the method described supra, a control nucleic acid is added to the sample and/or the purified nucleic acids. This control nucleic acid preferably is amplified by the same primer or primers as the target nucleic acid to be detected, to serve as a control for the amplification reaction, but is not necessarily. The control preferably is detected by a different probe or other method so it can be distinguished from a positive target result. Said control nucleic acid is in some embodiments a qualitative control nucleic acid, and in other embodiments a quantitative control nucleic acid, or both. The control nucleic acid is present in a precise, known quantity when serving as a quantitative control.

Qualitative detection of a bacterial nucleic acid in a sample is crucial e.g. for recognizing an infection by the bacteria of an individual or of a sample, such as donated blood or an organ for transplant. Therefore, one important requirement for an assay for detection, e.g., of a bacterial or viral nucleic acid is that false-negative or false-positive results be avoided wherever possible, since such results can lead to severe consequences with regard to treatment of the respective patients.

Thus, in an embodiment of the method described above, the presence of an amplification product of said control nucleic acid indicates an amplification occurring in the reaction mixture even in the absence of amplification products for said target nucleic acid.

On the other hand and in addition to mere detection of the presence or absence of a nucleic acid in a sample, it is often important to determine the quantity of said nucleic acid. As an example, stage and severity of an infectious disease may be assessed on the basis of the infectious agent load. Further, monitoring of any therapy requires information on the quantity or relative quantity of a pathogen present in an individual in order to evaluate the therapy's success.

Hence, an aspect of the invention is the method described above, further comprising the step of determining the quantity of the target nucleic acid comprising subgroups with sequence variations and/or individual mutations after and/or during detection.

For a quantitative assay, it may be desirable to introduce a quantitative standard nucleic acid serving as a reference for determining the absolute quantity of a target nucleic acid. Thus, a quantitative internal control nucleic acid may be added to the detection mix. Said control is particularly important for quantification of the test result but also for confirming the validity of a test result: The quantitative internal control nucleic acid would be detected in the case of both a negative result and a positive result with regard to the respective target nucleic acid. The quantitative internal control reaction would be required to perform within given settings or otherwise the test itself is considered to be inoperative. Quantitation can be effectuated either by referencing to an external calibration or by implementing an internal quantitative standard.

As known by the person skilled in the art, important values for characterizing a good quantitative assay are e.g. the assay's linearity or linear range (determined by quantitation of a dilution series of the target material with subsequent linear regression of the resulting curve), accuracy (correlation between nominal and experimentally determined/assigned values), inclusivity (equivalent and accurate quantification of genotypes/subtypes/mutants/isolates) and precision (standard deviation of the $\log_{10}$ transformed concentration result determined by variance component analysis using data generated from linearity studies).

For both quantitative and qualitative tests, properties like analytical sensitivity (described above in the context of LOD) or specificity (avoidance of false-positive results due to unspecific detection) also are significant parameters. It is shown in the examples herein that the method described above displays improved properties with regard to inclusivity as discussed above.

Further provided by the invention is a kit for amplifying and detecting a target nucleic acid that may be present in a sample, said target nucleic acid comprising a 16S sequence, said kit comprising amplification reagents comprising a DNA polymerase, nucleotide monomers, two or more primers for generating an amplicon and at least one detectable probe specific for a sequence portion of said amplicon. Such kits preferably also contain a cleaned reverse transcriptase and a control or standard nucleic acid. Preferred primers comprise at least a 10 contiguous nucleic acids from one or more of SEQ ID NOs:1-4, 9-10, 12-23, 25-26, and 28-32. Preferred probes are selected from the group consisting of SEQ ID Nos. 5-8, 11, 24, 27, 33-37, In an embodiment, the kit mentioned supra is a kit for amplifying and detecting a 16S nucleic acid of bacteria that may be present in a sample, said kit comprising amplification reagents comprising a polymerase, nucleotide monomers, primers for generating an amplicon and at least one detectable probe specific for a sequence portion of said amplicon, wherein said detectable probe comprises at least one sequence of at least 10 nucleotides from probes selected from the group consisting of SEQ ID NOs:5, 6, 7, 8, 11, 24, 27, 33, 34, 35, 36, and 37, or the respective complements thereof.

In another embodiment of the kit described above, the detectable probe specific for a sequence portion of said amplicon hybridizes to the amplicon. In an embodiment of the invention, the primers of the kit described above comprise more than one forward and/or reverse primer.

In an embodiment of the invention, the primers in the kit mentioned above comprise at least one element of SEQ ID NOs: 1, 2, 3, 4, 9, 10, 12, 13, 14, 15, 16, 17, 18, 19, 20, 21, 22, 23, 25, 26, 27, 28, 29, 30, 31, and 32, and optionally, probes of SEQ ID NOs: 5, 6, 7, 8, 11, 24, 27, 33, 34, 35, 36, and 37, as well as probes that could be designed based on known sequences so that all known bacterial species could be detected. Said primers are particularly useful for creating an amplicon detectable with the probes mentioned above. For sequences for which the probes included herein would not be expected to have sufficient sequence homology to allow detection, other methods such as gel electrophoresis, capillary electrophoresis, SyBr Green, or melting curve analysis would be examples of methods to detect such amplicons.

The advantages for said use and said kit are analogous to the ones described further supra in the context of the method according to the invention.

EXAMPLES

Example 1

In one example, a PCR reaction was conducted using a Takara EX Taq DNA polymerase Hot Start Version kit (Takara, cat no. RR006A) according to manufacture instructions. A potential bacterial DNA sample and primer pair SEQ ID NOs: 1 and 2 were used to produce an amplicon. This primer pair amplified a segment of the 16S gene. The results of the reaction are provided in FIG. 3 showing that no false positives were produced.

Example 2

Figure 4:
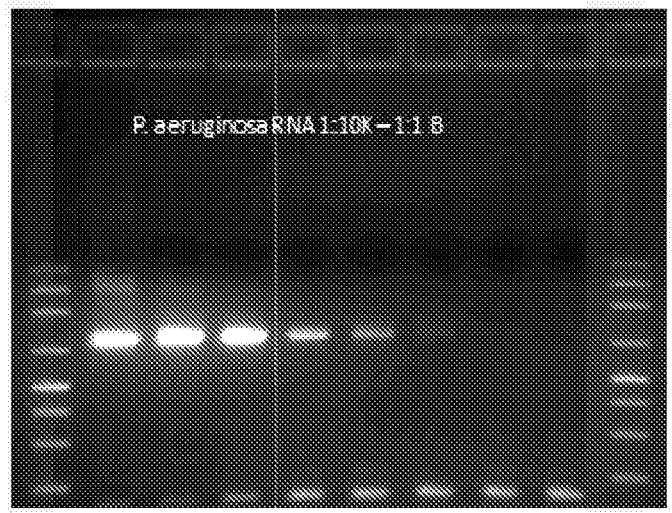
FIG. 4 is a photograph of a gel from an evaluation of PCR product made with real-time PCR using SEQ ID NOs 3 and 4, lanes 7 and 8.
Figure 5:
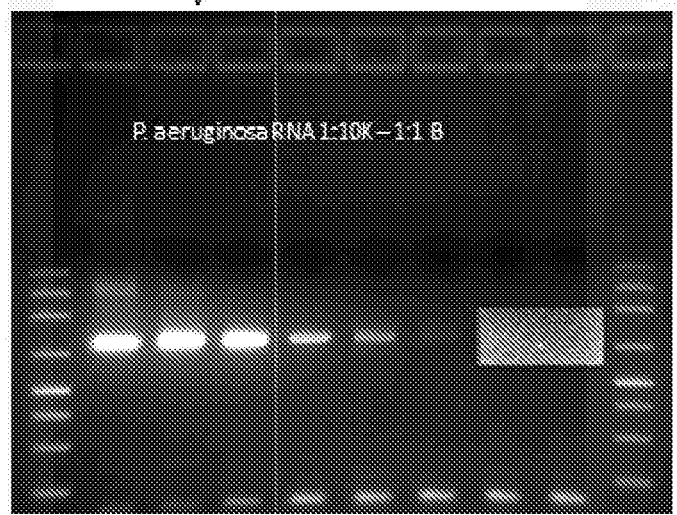
FIG. 5 is a photograph of a gel related to the evaluation shown in FIG. 4, but with the no RNA lanes enhanced to better show that no RNA is produced.

PCR reaction was conducted using a Takara EX Taq DNA polymerase Hot Start Version kit (Takara, cat no. RR006A) according to manufacture instructions. The sample and primer pair SEQ ID NOs: 3 and 4 were used to produce an amplicon. This primer pair amplified a segment of the 16S rRNA. The reaction also involved the use of reverse transcriptase. The results of the reaction are provided in FIGS. 3 and 4, showing that no false positives are produced.

PCR Reaction Mixture:

The master mixes evaluated consisted of the reference mastermix [$\frac{1}{10}^{th}$ volume 10× Ex Taq Buffer (proprietary mix), 0.2 mM of each dNTP, 1.25 units of Ex Taq, 0.2 mM each of primers and probe, template and water up to a final volume of 25 uls. which was supplemented with the different probes. The reference mastermix was prepared in a large batch.

PCR Reaction:

The following thermal cycling steps were applied:

| Duration | Temperature | Repetitions |
|---|---|---|
| 5 min | 95° C. | 1 |
| 40 cycles of 30 sec | 94° C. | |
| 30 sec | 58° C. | |
| 30 sec | 72° C. | |

Example 3

It has been discovered that for reactions involving reverse transcriptase, use of cleaned reverse transcriptase can provide an improved result without false positives. Cleaned reverse transcriptase may be produced using a clean manufacturing process, destruction or inactivation of contaminating nucleic acids by enzymatic reaction (e.g. endonucleases), physical, chemical or other means, and removal of contaminating nucleic acids by any means e.g. hybridization or any other binding method and then physical separating the contaminating nucleic acids from the RT enzyme.

Accordingly, in a specific embodiment, a cleaned reverse transcriptase is provided and used with the inventive methods, where contaminating sequences have been removed. Preferably, any nucleic acids that could be amplified by the probes in use should be removed or substantially removed. It should be borne in mind that cleaned reverse transcriptase does not necessarily have all nucleic acid removed, but at least those contaminating sequences that interfere with the PCR process and produce false positives.

Use of a clean reverse transcriptase allows one to use any and all "universal" or broad-based (or species specific) primers without a false positive from the Taq, not just the 2 primer pairs SEQ ID NOs 1 and 2 or 3 and 4. In particular, the clean reverse transcriptase may be used in conjunction with the linker isolation approach that is described in PCT application no.
PCT/US2012/000489.

Example 4

A PCR reaction is conducted using a Takara EX Taq DNA polymerase Hot Start Version kit (Takara, cat no. RR006A)

according to manufacture instructions. The sample and primer pair SEQ ID NOs: 25 and 26 are used to produce an amplicon of the target sequence of the 16S rRNA, using the following thermal cycling steps.

| Duration | Temperature | Repetitions |
|---|---|---|
| 5 min | 95° C. | 1 |
| 40 cycles of 30 sec | 94° C. | |
| 30 sec | 58° C. | |
| 30 sec | 72° C. | |

A cleaned reverse transcriptase is used. This cleaned reverse transcriptase is produced using a clean manufacturing process, and/or treatment of the enzyme with one or more endonucleases to destroy or inactivate any contaminating nucleic acids. Chemical or physical removal or inactivation methods also can be added to remove remaining contaminating nucleic acids, such as by hybridization or any other binding method, followed by physical separation of the contaminating or interfering nucleic acids from the reverse transcriptase enzyme. A cleaned reverse transcriptase allows use of "universal," broad-based or species specific primers without a false positive from the Taq. All patents, patent applications, patent publications, technical publications, scientific publications, and other references referenced herein and in the accompanying appendices are hereby incorporated by reference in this application to the extent not inconsistent with the teachings herein.

All technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method for detecting a target nucleic acid that may be present in a sample, said method comprising the steps of:
    a) contacting nucleic acids from said sample with amplification reagents comprising a DNA polymerase, nucleotide monomers, and two or more different primers specifically hybridizing to said target nucleic acid for generating an amplicon, wherein each of said primers comprise at least 10 contiguous nucleotides selected from SEQ ID NOs: 2-4, 9-10, 12, 14-23, 25-26, and 28-32 and performing an amplification reaction by incubating said nucleic acids with said amplification reagents for a period of time under conditions sufficient to amplify said target nucleic acid; and
    b) detecting the target nucleic acid by detecting an amplicon from said amplification reaction; wherein the presence of said amplicon indicates the presence of said target nucleic acid in said sample.

2. The method of claim 1, wherein the primers used in step (a) are selected from the group consisting of SEQ ID NOs: 2-4, 9-10, 12, 14-23, 25-26, and 28-32.

3. The method of claim 1, wherein said amplification reagents further comprise at least one detectable probe specifically hybridizing to a sequence portion of the amplicon.

4. The method of claim 1, wherein said detecting said amplicon in step (b) comprises detecting hybridization of a detectable probe to said amplicon.

5. The method of claim 4, wherein said detectable probe is selected from the group consisting of SEQ ID Nos. 5-8, 11, 24, 27, 33-37, or an effective fragment thereof.

6. The method of claim 1, wherein the sample comprises RNA and the amplification reagents further comprise a cleaned reverse transcriptase.

7. The method of claim 1, wherein the primers used in step (a) are selected from the group consisting of SEQ ID NOs: 25, 26, 28, 29, 30, 31, and 32.

8. The method of claim 1, wherein said amplification reaction in step (a) comprises real-time PCR amplification.

9. The method of claim 8, wherein said amplification reagents further comprise a sequence-specific DNA probe labelled with a fluorescent reporter.

10. The method of claim 8, wherein said amplification reagents further comprise a non-specific fluorescent dye that intercalates with a double-stranded DNA.

11. The method of claim 1, wherein said amplification reagents further comprise a control target nucleic acid.

12. The method of claim 11, wherein said control target nucleic acid is a quantitative control nucleic acid.

13. The method of claim 1, wherein said amplification reaction in step (a) comprises standard PCR.

14. The method of claim 1, wherein the amplification reagents further comprise a reverse transcriptase.

15. The method of claim 14, wherein the reverse transcriptase is a cleaned reverse transcriptase.

16. The method of claim 15, wherein the cleaned reverse transcriptase is produced by enzymatic, chemical, or physical treatment of a contaminated reverse transcriptase.

* * * * *